(12) United States Patent
Ogawa et al.

(10) Patent No.: US 7,378,394 B2
(45) Date of Patent: May 27, 2008

(54) SUSTAINED-RELEASE MICROPARTICLE PREPARATION OF HUMAN GROWTH HORMONE AND PROCESS FOR PRODUCING THEREOF

(75) Inventors: Yasuaki Ogawa, Kyoto (JP); Takao Fujii, Tokyo (JP); Yoko Miyamoto, Isehara (JP); Jun Niimi, Kawasaki (JP); Toshiyuki Ikoma, Tsukuba (JP); Junzo Tanaka, Tsukuba (JP)

(73) Assignees: GaleniSearch, Laboratories, Kanagawa (JP); Japan Science and Technology Agency, Saitama (JP); Independent Administrative Institution, National Institute For Materials Science, Ibaraki (JP)

( * ) Notice: Subject to any disclaimer, the term of this patent is extended or adjusted under 35 U.S.C. 154(b) by 99 days.

(21) Appl. No.: 10/554,574

(22) PCT Filed: Jun. 15, 2004

(86) PCT No.: PCT/JP2004/008344

§ 371 (c)(1),
(2), (4) Date: Oct. 27, 2005

(87) PCT Pub. No.: WO2004/112827

PCT Pub. Date: Dec. 29, 2004

(65) Prior Publication Data

US 2006/0258575 A1    Nov. 16, 2006

(30) Foreign Application Priority Data

Jun. 18, 2003    (JP) .............................. 2003-173410

(51) Int. Cl.
*A61K 38/27*    (2006.01)
*A61K 9/22*    (2006.01)
(52) U.S. Cl. ........................................ 514/12; 424/468
(58) Field of Classification Search ...................... None
See application file for complete search history.

(56) References Cited

U.S. PATENT DOCUMENTS 5,055,307 A    10/1991  Tsuru et al.
2006/0153930 A1 *  7/2006  Mizushima et al. ........ 424/604

FOREIGN PATENT DOCUMENTS

| JP | 11286403   | 10/1999 |
| JP | 2000239104 | 9/2000  |
| JP | 2002326960 | 11/2002 |
| JP | 2002348234 | 12/2002 |
| JP | 2004075662 | 3/2004  |

OTHER PUBLICATIONS

Gautier H. et al., "In vitro influence of apatite-granule-specific area on human growth hormone loading and release," *Journal of Biomedical Materials Research*, 1998, vol. 40, No. 4, pp. 606-613.
Guicheux J. et al., "Growth hormone-loaded macroporous calcium phosphate ceramic: In vitro biopharmaceutical characterization and preliminary in vivo study," *Journal of Biomedical Materials Research*, 1998, vol. 40, No. 4, pp. 560-566.
Guicheux J. et al., "Association of human growth hormone and calcium phosphate by dynamic compaction: In vitro biocompatibility and bioactivity," *Journal of Biomedical Materials Research*, 1997, vol. 36, No. 2, pp. 258-264.
Guicheux J. et al., "Apatite as carrier for growth hormone: In vitro characterization of loading and release," *Journal of Biomedical Materials Research*, 1997, vol. 34, No. 2, pp. 165-170.
Webster T. J. et al., "Hydroxylapatite with substituted magnesium, zinc, cadmium, and yttrium. II. Mechanisms of osteoblast adhesion," Journal of Biomedical Materials Research, 2002, vol. 59, No. 2, pp. 312-317.
Sogo, Y. et al., "The most appropriate (Ca+Zn)/P molar ratio to minimize the zinc content of ZnTCP/HAP ceramic used in the promotion of bone formation," *Journal of Biomedical Materials Research*, 2002, vol. 62, No. 3, pp. 457-463.
Ogawa, Y. et al., "A New Technique to Efficiently Entrap Leuprolide Acetate into Microcapsules of Polylactic Acid or Copoly(Lactic/Glycolic) Acid," *Chem. Pharm. Bull.* vol. 36, No. 3, 1998, pp. 1095-1103.
Johnson, O. L., et al., "A month-long effect from a single injection of microencapsulated human growth hormone," *Nature Medicine*, vol. 2, No. 7, Jul. 1996, pp. 795-799.
Yamaguchi, T. et al., "Ceramic Science Series 7 Bioceramics," Gihodo Shuppan Co., Ltd., 1984, pp. 7-9.

* cited by examiner

*Primary Examiner*—Manjunath Rao
*Assistant Examiner*—Ian Dang
(74) *Attorney, Agent, or Firm*—Price, Heneveld, Cooper, DeWitt & Litton, LLP

(57) ABSTRACT

Provided is a sustained-release microparticle preparation of a human growth hormone which combines biodegradability with sustained-release performance while avoiding the use of an organic solvent as much as possible, allows the sustained-release of a human growth hormone over 3 days or more and reduction in the initial burst release, can contain a human growth hormone at 10% or more, can quantitatively adsorb and encapsulate a human growth hormone at up to 20%, and has excellent dispersion and needle penetration properties. A process for producing the sustained-release microparticle preparation of a human growth hormone is also provided. The sustained-release microparticle preparation comprises a porous apatite derivative, a human growth hormone, and a water-soluble divalent metal compound.

4 Claims, No Drawings

SUSTAINED-RELEASE MICROPARTICLE PREPARATION OF HUMAN GROWTH HORMONE AND PROCESS FOR PRODUCING THEREOF

TECHNICAL FIELD

The present invention relates to a sustained-release microparticle preparation of a human growth hormone comprising, as a base, fine particles of a porous apatite derivative that is bioerodible in the living body and to a process for producing THEREOF.

BACKGROUND ART

Investigation has heretofore been made on injections that provide the sustained release of a water-soluble drug for a long time, most of which comprise poly-lactic-co-glycolic acid (PLGA) as a base (see e.g., Japanese Patent Laid-Open Nos. 11-286403, 2000-239104, and 2002-326960). Alternatively, sustained-release microcapsules that contain a human growth hormone (hGH) and comprise PLGA as a base have been reported (see e.g., Nature Medicine, 2: 795-799, 1996). Sustained-release microcapsules that contain leuprorelin, a LHRH agonist, and comprise PLGA as a base have also been reported (see e.g., Chemical Pharmaceutical Bulletin, 36: 1095-1103, 1988). PLGA is a biodegradable base that hydrolyzes and eliminates in the living body, and this property is preferable for a base of an injection.

Although an organic solvent that dissolves PLGA is generally used for producing a sustained-release preparation with PLGA, hGH is denatured in the organic solvent and a portion thereof is inactivated. Such reduction in activity not only impairs efficacy but poses the risk of adversely affecting a living body. Furthermore, hGH is highly soluble in water, and the use of a PLGA preparation inevitably results in the excessive release of hGH in the early stage after administration. In addition, although the use of hydrogel or the like has been reported, the hydrogel is difficult to administer by means of a typical injection. That is, a thick needle that permits the gel to pass therethrough must be used and is unfavorable for patients. Sustained-release particles using hydroxyapatite and a human growth hormone that is a bioactive drug have already been reported (see e.g., H. Gautier et al., Journal of Biomedical Material Research, 40,606-613,1998; and J. Guicheux et al., Journal of Biomedical Material Research, 34, 165-170, 1997). However, any of the sustained-release particles are two-component systems where apatite has a large particle size of 40 to 80 μm or 200 μm and is therefore difficult to inject. Moreover, their in vivo sustained-release effect is unknown. Besides, the amount of hGH adsorbed into the apatite particle (the amount of hGH encapsulated) was as low as 1% or less.

For a sustained-release preparation of hGH, a material having so-called biodegradability or a property of eliminating in the living body, which eliminates from a living body about the end of the release of a drug after administration, must be selected as a sustained-release base. In its production, a sustained-release preparation is prepared with the use of an organic solvent avoided as much as possible for preventing the denaturation of hGH. At the same time, the initial burst release (the release of an excessive drug in the early stage after administration) of hGH must be small. Moreover, the amount of a drug encapsulated in a microparticle preparation is brought to 10% or more by weight. The preparation capable of being easily administered with a thin injection needle must be prepared, wherein the duration of the sustained-release of a drug extends at least 3 days or more.

The present inventors have found that the use of fine particles of a porous apatite derivative for solving these problems achieves a preparation combining biodegradability with sustained-release performance, without the use of an organic solvent. The present inventors have further found that the use of hGH in combination with a water-soluble divalent metal compound achieves the sustained-release of hGH over at least 3 days or more and reduces initial burst release. In addition, the present inventors have found that a hGH content of 10% or more can be attained and hGH up to 20% can quantitatively be adsorbed and contained, and also found that the obtained fine granular preparation has excellent dispersion and needle penetration properties and easily passes through a 27 G injection needle.

Thus, an object of the present invention is to provide a sustained-release fine granular preparation of a human growth hormone which combines biodegradability with sustained-release performance while avoiding the use of an organic solvent as much as possible, allows the sustained release of a human growth hormone over 3 days or more and reduction in the initial burst release, can contain a human growth hormone at 10% or more, can quantitatively adsorb and include a human growth hormone at up to 20%, and has excellent dispersion and needle penetration properties. The present invention is also intended to provide a process for producing the sustained-release fine granular preparation of a human growth hormone.

DISCLOSURE OF THE INVENTION

A sustained-release microparticle preparation of a human growth hormone comprises a porous apatite derivative, and a human growth hormone and a water-soluble polyvalent metal compound contained in the porous apatite derivative. The water-soluble polyvalent metal compound includes zinc chloride, calcium chloride, calcium hydroxide, iron chloride, iron hydroxide, cobalt chloride, aluminum chloride, and zinc acetate. Among others, a water-soluble divalent metal compound is most preferable. The water-soluble divalent metal compound is preferably a zinc compound and a calcium compound, most preferably zinc chloride. In addition, zinc acetate, calcium chloride, and so on are preferable.

It is preferred that the porous apatite derivative should be a porous apatite derivative in which a portion of calcium as a constituent of hydroxyapatite is substituted by zinc.

It is also preferred that the substitutional atomic ratio of zinc to calcium in the porous apatite derivative should be 0.1 to 2.0.

Moreover, it is preferred that the porous apatite derivative should have a human growth hormone content of 10 to 40%.

A process for producing the sustained-release microparticle preparation of a human growth hormone of the present invention comprises: stirring and dispersing fine particles of a porous apatite derivative in water containing a human growth hormone; after the water is infiltrated into the porous apatite derivative, adding an aqueous solution containing a water-soluble divalent metal compound to infiltrate the water-soluble divalent metal compound into the porous apatite derivative; and then adding an additive such as a stabilizer, followed by freeze-drying or vacuum-drying.

The sustained-release microparticle preparation of hGH thus obtained is a sustained-release microparticle preparation of hGH comprising a porous apatite derivative (a porous apatite derivative in which a portion of calcium as a constituent of hydroxyapatite is substituted by any of other metals, preferably by zinc) slowly soluble in water, hGH, and an aqueous divalent metal compound. More preferred is the sustained-release microparticle preparation of hGH in which the ratio of zinc to calcium in the porous apatite derivative soluble in water is 0.1 to 2.0, while the water-soluble divalent metal compound is a zinc compound.

In a basic process for producing the sustained-release microparticle preparation of hGH, fine particles of a porous apatite derivative are dispersed in water containing hGH and, after the water is sufficiently infiltrated into the porous apatite derivative, an aqueous solution containing a water-soluble divalent metal compound is added to sufficiently infiltrate the water-soluble divalent metal compound into the porous apatite derivative. Then, an appropriate additive such as a stabilizer is added, followed by freeze-drying or vacuum-drying to thereby obtain a powder of a sustained-release microparticle preparation comprising, as a base, the porous apatite derivative containing the hGH. When actually administered, this powder is dispersed in an appropriate dispersion medium and administered, for example, subcutaneously or intramuscularly.

When the desorption of the encapsulated hGH is measured by dispersing the microparticles thus obtained in a large amount of purified water at room temperature, the hGH of an amount below a certain amount with respect to porous apatite derivatives was not desorbed, depending on the types of the porous apatite derivatives. That is, the hGH is probably infiltrated and adsorbed into the fine pores of the porous apatite derivatives.

The fine particles of a porous apatite derivative used in the present invention can be obtained by a known method. The method includes a method described in, for example, T. Yamaguchi, H. Yanagida, A. Makishima, H. Aoki, Ceramic Science Series 7 Bioceramics, GIHODO SHUPPAN Co., Ltd., pp. 7-9, 1984. The most preferable porous apatite derivative is any of those in which a portion of Ca is substituted by zinc (Zn) in the composition of hydroxyapatite. The ratio of zinc which substitutes calcium in hydroxyapatite (the ratio of Zn atoms substituted to Ca 10 atoms of hydroxyapatite) is preferably 0.1 to 5.0, more preferably 0.5 to 2.0. In this case, the velocity of the hydroxyapatite eliminating in the living body differs depending on the ratio of (Ca+Zn)/P. If the ratio is smaller than 1.67, the hydroxyapatite is more likely to be soluble in water, that is, the velocity of the hydroxyapatite eliminating in the living body is accelerated. It is preferred that the ratio of (Ca+Zn)/P should fall within the range of 1.67 to 1.51. A lower treatment temperature at which hydroxyapatite is produced renders the hydroxyapatite more soluble in water, that is, accelerates the velocity of the hydroxyapatite eliminating in the living body. The treatment temperature used is room temperature to 800° C., preferably 150° C. to 600° C. More preferable is a treatment temperature of 150° C. to 400° C. If hydroxyapatite is treated at 800° C. or higher, the hydroxyapatite does not eliminate in the living body. If hydroxyapatite is treated at 100° C. or lower, particles thereof tend to agglomerate together and are therefore difficult to administer by a typical injection. The particle size of each fine particle can be controlled by a treatment temperature and can be used in the range of 0.1 µm to 100 µm. Of these sizes, preferred is 0.1 µm to 20 µm. The fine particles having a size of 0.2 µm to 10 µm can be preferably used.

A porous apatite derivative having a larger ratio of Zn which substitutes calcium in the porous apatite derivative to the porous apatite derivative had a much larger ratio of hGH adsorbed into the porous apatite derivative. This is attributed to the specific surface and porosity of the porous apatite derivative that are significantly increased by allowing zinc to be substituted. The larger ratio of hGH adsorbed is preferred because the gross amount of the sustained-release preparation administered is rendered smaller. The preferred ratio of hGH adsorbed differs depending on the duration of the sustained-release of the hGH and however, is generally 2 to 30% by weight with respect to the porous apatite derivative. Of these rates, 5 to 25% by weight is preferably used. More preferred is any of those adsorbing 10% or more by weight of hGH therein.

The water-soluble divalent metal compound that is added after the hGH is adsorbed into the porous apatite derivative is preferably a Zn or Ca compound. Of them, the Zn compound is most preferable. The amount of its usage is preferably in the range of 10 to 100% by weight on a zinc chloride basis with respect to the porous apatite derivative and more preferably in the range of 20 to 70% by weight for sufficiently maintaining the sustained-release property. A chloride or a salt of an organic acid is preferably selected as the water-soluble divalent metal compound used. Examples thereof include zinc chloride, zinc acetate, and calcium chloride.

The particle size of the sustained-release microparticle preparation finally obtained may be a size that allows the preparation to pass through an injection needle used in typical administration. In reality, the smaller size an injection needle has, the less a patient is scared. It is preferred that the sustained-release microparticle preparation should pass through an injection needle with a thickness of 25 G or smaller (the greater the number is, the thinner an injection needle gets) defined by the international standard that specifies the thickness of an injection needle. It is more preferable that the sustained-release microparticle preparation should pass through an injection needle with a thickness of 27 G or smaller. For this reason, a sustained-release microparticle preparation having a smaller particle size is more preferable. However, a sustained-release microparticle preparation having a particle size rendered small to the extreme reduces the amount of a drug retained therein and the increases initial burst release of a drug. Thus, the particle size is preferably 0.5 µm to 20 µm, more preferably 0.5 µm to 10 µm. The duration of the sustained release of the hGH-containing sustained-release microparticle preparation thus obtained can be controlled by a temperature at which the hydroxyapatite(HAP) derivative is treated and the amount of usage of the divalent metal compound, allowing the sustained-release of hGH over 3 days or more. The sustained-release of hGH over 1 week or more is made possible and is preferred in practical ways.

EXAMPLES

The present invention will be described hereinafter in detail with reference to Examples and however, is not intended to be limited to these Examples by any means.

Example 1

To 50 mg of a porous HAP or a porous apatite derivative (HAP-Zn-0.5: 0.5 parts zinc atom with respect to 9.5 parts calcium atom) treated at 180° C., a human growth hormone (hGH) solution (25 mg/ml) desalted with a PD-10 column (Amersham Pharmacia) was added (200 µL to the HAP and 700 µL to the HAP-Zn-0.5) and stirred for 1 minute with a touch mixer. Next, water was added to each of the solutions to adjust the final volume to 2.5 mL and further stirred for 1 minute. After being left undisturbed for 3 minutes, the mixtures were centrifuged at 3,000 rpm for 3 minutes, and the resulting precipitations were supplemented with 2.5 mL of water, respectively, and stirred for 1 minute. The mixtures were centrifuged again at 3,000 rpm for 3 minutes, and the resulting precipitations were supplemented with 0.333 mL (25 µmol of zinc chloride), 1 mL (75 µmol of zinc chloride), and 2 mL (150 µmol of zinc chloride) of an aqueous solution of 10.2 mg/mL zinc chloride (Wako Pure Chemical Industries, Ltd., Osaka, Japan), respectively, and stirred with a touch mixer, followed by freeze-drying to prepare samples in a powder form. A sample used as a control was prepared by adding water instead of a zinc chloride solution. The volume mean diameters of the obtained samples ranged from 6 to 8 µm with the maximum being 20 µm. hGH contents in the obtained HAP-hGH and HAP-Zn-0.5-hGH samples were quantified with the micro BCA protein assay kit (Pierce). In addition, the in vitro release properties of the obtained samples were compared. The release properties were evaluated by the following procedures: 5 mg of each of the obtained samples was accurately weighed, then supplemented with 0.250 mL of PBS (phosphate buffered saline), and stirred at 37° C.; the supernatants were periodically collected by centrifugation at 3,000 rpm for 3 minutes, and the amounts of hGH released into the supernatants were quantified by gel filtration HPLC analysis (TOSO G2000SW-x1) to calculate the percentage of the amount of hGH released to the gross amount of hGH contained in each of the samples. This result is shown in Table 1. The samples supplemented with zinc chloride had remarkable reduction in the amount of hGH released into PBS in response to the amount of zinc chloride added, as compared to the sample prepared as a control in which only hGH was allowed to act on HAP.

TABLE 1

Effect of zinc chloride on in vitro release property of microparticle preparations of porous apatites adsorbing hGH therein

| | Percentage of cumulative amount of hGH released into PBS to gross amount of hGH (%) | | | |
|---|---|---|---|---|
| | 1 hr | 2 hr | 4 hr | 24 hr |
| HAP-hGH-no zinc chloride | 35 | 37.7 | 38.8 | 43.9 |
| HAP-hGH-zinc chloride-25 µmol | 0 | 0 | 0.093 | 0.27 |
| HAP-hGH-zinc chloride-75 µmol | 0 | 0 | 0 | 0 |
| HAP-hGH-zinc chloride-150 µmol | 0 | 0 | 0 | 0 |
| HAP-Zn-hGH-zinc chloride-188 µmol | 0 | 0 | 0 | 0 |

Example 2

To 10 mg of each of three porous apatite derivatives in which a portion of calcium in HAP was substituted by zinc (HAP-Zn-0.1:0.1 parts zinc atom with respect to 9.9 parts calcium atom; HAP-Zn-0.5: 0.5 parts zinc atom with respect to 9.5 parts calcium atom; and HAP-Zn-1.0:1.0 parts zinc atom with respect to 9.0 parts calcium atom) and HAP (all of which are treated at 180° C.), 50 µL, 100 µL, 200 µL, and 400 µL of a hGH solution (10 mg/ml) desalted with a PD-10 column (Amersham Pharmacia) were added, respectively, and stirred for 1 minute with a touch mixer. Water was further added to each of the solutions to adjust the final volume to 500 µL and stirred for 1 minute with a touch mixer. After being left undisturbed for 3 minutes, the mixtures were centrifuged at 3,000 rpm for 3 minutes, and the amounts of hGH contained in the resulting precipitations were quantified with the micro BCA protein assay kit (Pierce) to compare the amount of hGH in each of the samples. This procedure allows the detection of only hGH adsorbed into the porous apatite derivatives for each of the samples. The result is shown in Table 2. The volume mean diameter of the obtained samples ranged from 6 to 8 µm with the maximum being 20 µm. The porous apatite derivatives undergoing zinc substitution had significant increase in the amount of hGH adsorbed, as compared to the HAP undergoing no zinc substitution. Moreover, the amount of hGH adsorbed greatly increased as the proportion of zinc introduced into the porous apatite derivative increased. When 10 mg of the HAP-Zn-1.0 was used and the amount of hGH charged is not more than 2 mg, the whole hGH charged was adsorbed therein. At this time, a hGH content is 20%.

TABLE 2

Comparison of amounts of hGH adsorbed into porous apatite derivatives

| Amount of hGH | Amount of hGH adsorbed (mg/HAP 10 mg) | | | |
|---|---|---|---|---|
| charged (mg) | HAP | HAP-Zn-0.1 | HAP-Zn-0.5 | HAP-Zn-1.0 |
| 0.5 | 0.51 | 0.53 | 0.52 | 0.51 |
| 1 | 0.96 | 1.05 | 1.06 | 1.02 |

TABLE 2-continued

Comparison of amounts of hGH adsorbed
into porous apatite derivatives

| Amount of hGH charged (mg) | Amount of hGH adsorbed (mg/HAP 10 mg) | | | |
|---|---|---|---|---|
| | HAP | HAP-Zn-0.1 | HAP-Zn-0.5 | HAP-Zn-1.0 |
| 2 | 1.25 | 1.49 | 1.87 | 1.92 |
| 4 | 1.52 | 1.94 | 2.74 | 2.91 |

Example 3

To 50 mg of HAP or HAP-Zn-0.5, a hGH solution (10 mg/ml) was added (0.5 mL to HAP and 1.75 mL to HAP-Zn-0.5) and stirred for 1 minute with a touch mixer. Next, water was added to each of the solutions to adjust the final volume to 2.5 mL and further stirred for 1 minute with a touch mixer. After being left undisturbed for 3 minutes, the mixtures were centrifuged at 3,000 rpm for 3 minutes, and the resulting precipitations were supplemented with 2.5 mL of water, respectively, and stirred again for 1 minute. The mixtures were centrifuged again at 3,000 rpm for 3 minutes, and the resulting precipitations were supplemented with 1 mL (75 µmol) (for HAP-hGH) and 2.25 ml (188 µmol) (for HAP-Zn-hGH) of a aqueous solution of 10.2 mg/mL zinc chloride (Wako) and stirred with a touch mixer, followed by freeze-drying to prepare samples (represented by HAP-hGH-zinc chloride and HAP-Zn-hGH-zinc chloride, respectively). A sample used as a control is prepared by adding water instead of a zinc chloride solution (represented by HAP-hGH or HAP-Zn-hGH). All of the volume mean diameters of the obtained samples ranged from 6 to 8 µm when measured with a coulter counter. hGH contents in the obtained HAP-hGH and HAP-Zn-hGH samples were quantified with the micro BCA protein assay kit (Pierce) The HAP-hGH, the HAP-hGH-zinc chloride, and the HAP-Zn-hGH-zinc chloride were suspended in 0.5% CMC-Na, 5% mannitol, and 0.1% Tween 80. And 10 IU/kg (1 IU: 0.35 mg) of each resulting suspension was subcutaneously administered to the back of a male SD rat. In addition, hGH dissolved in the same solvent was administered as a control.

Table 3 shows the dispersion and needle penetration properties of each of the preparations at the time of administration. The HAP-hGH had poor dispersion property and did not pass through a 27 G injection needle. In contrast, the preparations supplemented with the HAP-Zn-hGH and zinc chloride were improved in dispersion and needle penetration properties. Concerning a needle penetration properties for a 27 G injection needle, particularly the HAP-Zn-hGH-zinc chloride passed through the 27 G injection needle more easily than the other two preparations that passed therethrough.

After 1, 2, 4, and 8 hours post-administration and subsequently on every 1 day, blood was collected from the tail vein the rats to measure the blood level of hGH using the E test "TOSOH" II (HGH) (a full automatic EIA device AIA-6000, TOSOH Corp). This result is shown in Table 4. When a hGH solution was administered, hGH quickly eliminated from blood and no hGH was detected in blood after 8 hours post-administration. In the case of the HAP-hGH, high burst was observed in the early stage. On the other hand, in the case of the HAP-hGH-zinc chloride, initial burst was considerably reduced, and sustained-release effect was observed over 1 week. The HAP-Zn-hGH-zinc chloride was confirmed to have increase in a hGH content and increase in the sustainability of the blood level of hGH. Moreover, when the preparation remaining in the hypodermis on 20 days post-administration was visually observed, it was observed that the most parts thereof disappeared.

TABLE 3

Comparison of dispersion needle penetration properties of microparticles preparations of porous apatites containing hGH

| | hGH content | Dispersion | Needle penetration properties | | |
|---|---|---|---|---|---|
| | (% by weight) | property | 23G | 25G | 27G |
| HAP-hGH | 7.6 | X | ○ | Δ | X |
| HAP-Zn-hGH | 22.3 | ○ | ○ | ○ | ◎ |
| HAP-hGH-zinc chloride | 5.9 | ○ | ○ | ○ | ○ |
| HAP-Zn-hGH-zinc chloride | 16.2 | ◎ | ○ | ○ | ◎ |

TABLE 4

Time courses in blood level of hGH after subcutaneous administration of fine granular preparations of porous apatites to rats

| | hGH content in preparation | Blood level of hGH (ng/mL) | | | | | | | | | | |
|---|---|---|---|---|---|---|---|---|---|---|---|---|
| | (% by weight) | 1 hr | 2 hr | 4 hr | 8 hr | 1 day | 2 day | 3 day | 4 day | 5 day | 6 day | 7 day |
| hGH | | 249 | 139 | 0.5 | 0 | | | | | | | |
| HAP-hGH | 7.6 | 301 | 326 | 224 | 46.3 | 2.8 | 0.9 | 0.37 | 0.14 | 0.11 | 0.05 | 0.02 |
| HAP-Zn-hGH | 22.3 | 343 | 294 | 170 | 27.3 | 1.41 | 0.86 | 0.35 | 0.15 | 0.08 | 0.02 | 0.02 |
| HAP-hGH-zinc chloride | 6.6 | 5 | 16.9 | 51.3 | 99.7 | 11.1 | 2.03 | 1.49 | 0.65 | 0.4 | 0.16 | 0.2 |
| HAP-Zn-hGH-zinc chloride | 16.2 | 4 | 11.7 | 26.4 | 49.1 | 11.8 | 2.81 | 1.32 | 0.78 | 0.43 | 0.32 | 0.18 |

(Average value of n = 3 for each time)

The invention claimed is:

1. A sustained-release microparticle preparation of human growth hormone characterized in that human growth hormone and a water-soluble divalent metal compound are adsorbed to a zinc-containing porous hydroxyapatite which is formed by partially substituting calcium atoms of porous hydroxyapatite with zinc.

2. The sustained-release microparticle preparation of a human growth hormone according to claim 1, characterized in that the water-soluble divalent metal compound is zinc chloride.

3. The sustained-release microparticle preparation of a human growth hormone according to claim 1, characterized in that the number of atoms of zinc contained in the zinc-containing porous hydroxyapatite is 0.1 to 2.0 relative to 10 atoms of calcium of the porous hydroxyapatite.

4. The sustained-release microparticle preparation of a human growth hormone according to claim 1, characterized in that the content of human growth hormone in the zinc-containing porous hydroxyapatite is 10 to 40% by weight.

* * * * *